(12) United States Patent
Fischell

(10) Patent No.: US 8,562,573 B1
(45) Date of Patent: Oct. 22, 2013

(54) GUIDING CATHETER FOR ACCESSING THE RENAL ARTERIES

(75) Inventor: Robert E. Fischell, Dayton, MD (US)

(73) Assignee: Fischell Innovations, LLC, Fair Haven, NJ (US)

(*) Notice: Subject to any disclaimer, the term of this patent is extended or adjusted under 35 U.S.C. 154(b) by 0 days.

(21) Appl. No.: 13/488,526

(22) Filed: Jun. 5, 2012

(51) Int. Cl.
*A61M 25/00* (2006.01)
*A61M 29/00* (2006.01)
*A61M 5/178* (2006.01)

(52) U.S. Cl.
USPC ............... 604/264; 604/164.1; 604/96.01; 604/104

(58) Field of Classification Search
USPC ........... 604/164.1, 264, 96.01, 523–525, 528, 604/104
See application file for complete search history.

(56) References Cited

U.S. PATENT DOCUMENTS

| 5,389,090 | A | 2/1995 | Fischell et al. |
| 5,836,895 | A * | 11/1998 | Ramsey, III ............... 600/593 |
| 2007/0299403 | A1* | 12/2007 | Crowe et al. ............ 604/170.03 |
| 2010/0022944 | A1* | 1/2010 | Wilcox ..................... 604/22 |

* cited by examiner

*Primary Examiner* — Nicholas Lucchesi
*Assistant Examiner* — Rebecca E Eisenberg
(74) *Attorney, Agent, or Firm* — Rosenberg, Klein & Lee

(57) ABSTRACT

An elongated hollow tube guiding catheter forming a portion of a guiding catheter includes a proximal end, distal end, and distal section. The distal section includes a curved section and a straight section. The curved and straight sections are shaped for facilitating introduction and retention of the catheter into the ostium of a renal artery. The system includes a dilator inserted into the catheter hollow tube with a curved distal section of the dilator opposingly extending opposite the curved distal section of the guiding catheter hollow tube. The guiding catheter includes a side arm positioned near the guiding catheter's proximal end with a multi-way stop cock fixedly attached onto a proximal end of the side arm tube.

18 Claims, 4 Drawing Sheets

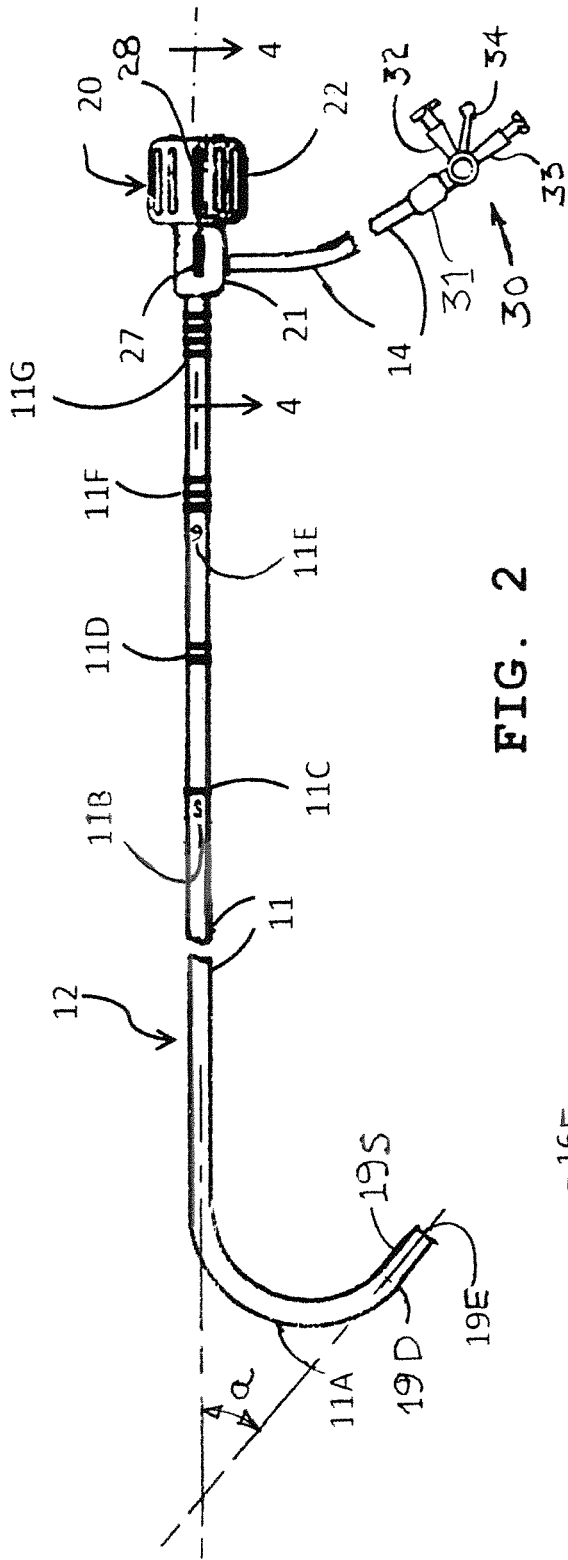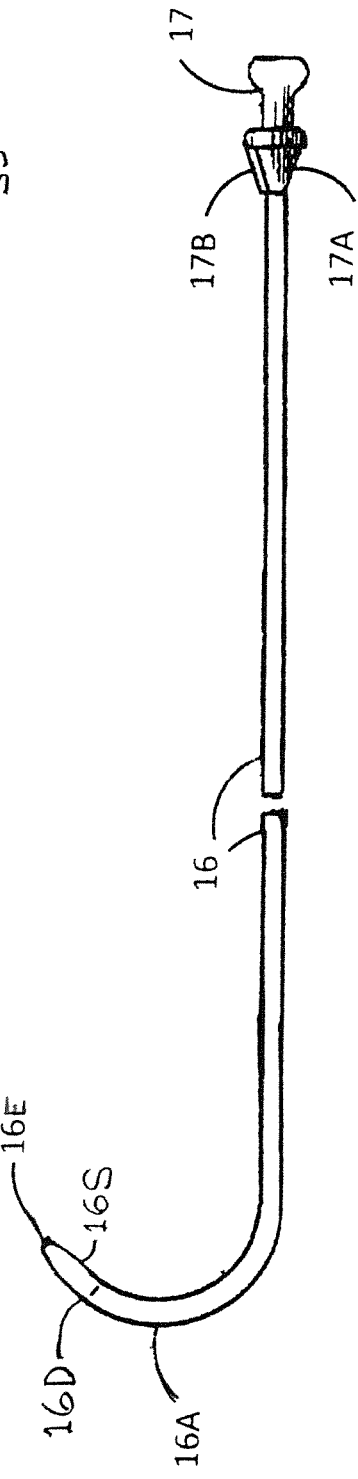
FIG. 2
FIG. 3

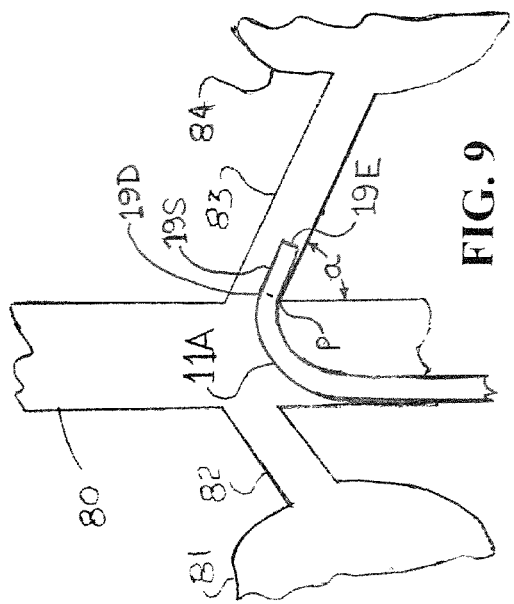
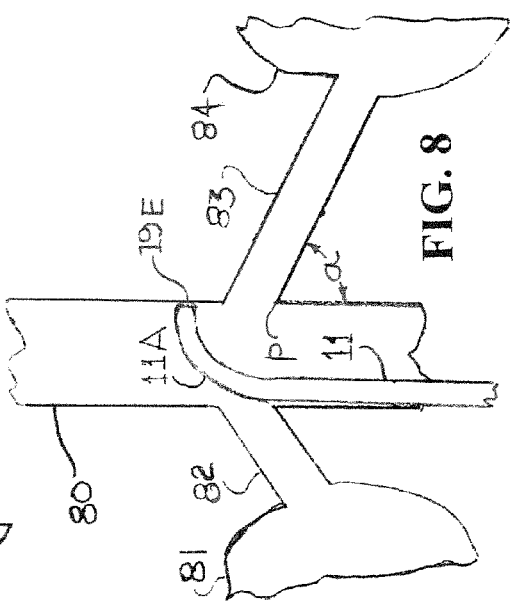
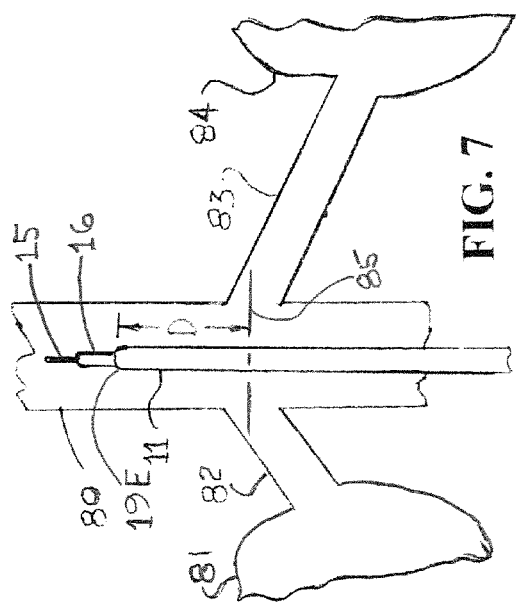

GUIDING CATHETER FOR ACCESSING THE RENAL ARTERIES

FIELD OF USE

This invention is in the field of methods and devices for accessing the renal arteries for the treatment of high blood pressure.

BACKGROUND OF THE INVENTION

There are now several catheters being developed by several different companies whose goal is to perform renal nerve denervation to reduce the blood pressure for hypertensive patients. Therefore, it will become increasingly important over the next several years to create improved means for renal denervation catheters to access the renal arteries.

The current practice for accessing the renal arteries is to first use an arterial access needle puncture at the groin, and then a guide wire is placed through that needle into the femoral artery. The needle is then removed while the guide wire remains in place in the femoral artery at the groin. An introducer sheath with dilator would then be advanced over the guide wire and into the lumen of the femoral artery. The dilator and the guide wire would then be removed and a guiding catheter would be advanced through the introducer sheath until its distal end would be placed into a renal artery. A catheter for renal denervation could then be advanced through the guiding catheter and it would be used to kill a section of the renal nerves that surround the renal artery thus permanently lowering the blood pressure of a patient that is hypertensive.

The renal denervation catheters require a fairly large diameter guiding catheter; typically 6, 7 or 8 French size. Since the outer diameter of the sheath through which the guiding catheter is inserted is typically 2 to 3 French sizes larger than the outer diameter of the guiding catheter, a fairly large diameter hole must be made through the wall of the femoral artery. These larger size holes can lead to excessive bleeding at the groin after the guiding catheter and the sheath are removed.

At this time, all guiding catheters designed for accessing the renal arteries terminate at their proximal end with a Luer fitting. To perforin an intra-arterial procedure with any existing guiding catheter, it is necessary to attach a Tuohy-Borst "Y" adaptor onto the Luer fitting at the guiding catheter's proximal end. The introducer sheath and Tuohy-Borst "Y" adaptor are each components that require additional time for the interventional cardiologist to properly place, and they add to the cost of performing intra-arterial procedures. Also, the introducer sheath through which the guiding catheter is inserted typically must have a three-way stopcock attached to a Luer fitting on a side arm tube that is located near the proximal end of the introducer sheath. The additions of a Tuohy-Borst "Y" adaptor to the guiding catheter and adding a three-way stopcock to the side tube of the introducer sheath adds additional cost and time to any procedure for accessing the renal artery. If a means for accessing the renal artery could be accomplished without requiring an introducer sheath and without requiring the additional parts of a Tuohy-Borst "Y" adaptor and a three-way stopcock, the procedure could be done in less time and at a lower cost.

In U.S. Pat. No. 5,389,090, Fischell et al describe an improved guiding catheter that is particularly useful for accessing the coronary arteries. However, there are no specific features of that invention that are specifically devoted for improved access for the renal arteries. Specifically, the invention described in the '090 patent does not teach markings on the shaft of the guiding catheter to assist in the placement of that guiding catheter into the renal arteries. The '090 patent also fails to teach the importance of a side arm tube that lies in the same plane as does the curve at the distal section of the guiding catheter, which feature enables the operator to have the correct azimuth angle for placement of the distal end of the guiding catheter into and through the ostium of the renal artery. Still further, the '090 patent fails to teach a three-way stopcock formed integral with the side arm tube at the guiding catheter's proximal end that precludes the need for the operator to open a separate package to attach that device to the guiding catheter. A guiding catheter design that would not require the use of an introducer sheath and would have a Tuohy-Borst fitting and a three-way stopcock each formed integral with the guiding catheter at its proximal end would result in savings of both time and cost for the procedure to access the renal arteries.

SUMMARY OF THE INVENTION

The present invention is an improved guiding catheter designed explicitly to access the renal artery. This renal artery guiding catheter eliminates the need for: 1) an introducer sheath; 2) a separate Tuohy-Borst "Y" adaptor; and 3) a separate three-way stopcock. By this means, the present invention provides a means and method for reducing the time and expense for performing renal artery procedures. Furthermore, the guiding catheter with straightening dilator as described herein allows the hole in the wall of the femoral artery to be approximately 2 to 3 French sizes smaller in diameter as compared to the hole that would be created if an introducer sheath is also used, thus decreasing the possibility of bleeding at the groin. Still further by making the curve at the distal section of the shaft of the guiding catheter to be coplanar with the guiding catheter's side arm tube, the interventional cardiologist can more easily place the distal end of the guiding catheter into and through the ostium of the renal artery. Additionally, explicit markings along the tube of the guiding catheter allow the interventional cardiologist to more accurately place the distal end of the guiding catheter into the aorta prior to removing the dilator and guide wire from the guiding catheter. Still further, the shape of the distal section of this special guiding catheter allows entry of a straight section at the distal end of the guiding catheter to be advantageously placed into the renal artery irrespective of the angle that the renal artery makes with the aorta.

The advantages of the present invention are accomplished by utilizing a dilator that has a curved distal section placed 180 degrees opposite from the curve at the guiding catheter's distal section, which opposing curve of the dilator is used to initially straighten the curved distal section of the renal artery guiding catheter as it is advanced through the patient's arterial system. In this way, the dilator straightens the guiding catheter so that it can be used like an introducer sheath to enter the femoral artery by being advanced over a previously placed guide wire. Once the distal ends of the guide wire, dilator and guiding catheter are placed just beyond the ostium of a renal artery, the dilator and guide wire are withdrawn which allows a distal section of the guiding catheter to assume its normally bent shape. By pulling the guiding catheter back down the aorta, the cardiologist can then place the guiding catheter's distal end into and through the ostium of either the right or the left renal artery. Any one of several well-known procedures can then be performed including denervation of the renal nerves, angiography, balloon angioplasty, and atherectomy or stent placement. The unique design of the distal section of the guiding catheter allows a short straight section at that curves distal end to be placed into the renal artery irrespective of the angle that the renal artery makes with the aorta. This design feature precludes the need for making a variety of shapes for different guiding catheters that would otherwise be required to access renal arteries that make different entry angles relative to the aorta. Another means for expressing this advantage is that only one product code is required to be manufactured by the company that makes this product, which product will include a guiding catheter having a distal straight section that is able to readily enter a renal artery irrespective of the angle that that renal artery makes with the aorta. A marketing advantage for the present invention is that the manager of a cath lab will prefer to have a reduced inventory of guiding catheters to access the femoral artery. Therefore, having only a single product code would provide that desired goal of a reduced inventory for this renal artery guiding catheter product.

The guiding catheter of the present invention utilizes a Tuohy-Borst fitting that is formed integral with the guiding catheter and a side arm tube all placed at the guiding catheter's proximal end. This capability obviates the need for attaching a separate Tuohy-Borst "Y" adaptor at the guiding catheter's proximal end to accomplish arterial access with minimum bleeding. The guiding catheter's Tuohy-Borst fitting could be tightened around guide wires or the shaft of catheters that are advanced through the guiding catheter.

The side arm tube, also located at the proximal end of the guiding catheter. could terminate in a female Luer fitting as described in the '090 patent, or more advantageously it could have a three-way stopcock formed integral with the side arm tube at the tube's proximal end. That three-way stopcock could be attached to a manifold for the introduction of saline solution, contrast medium, medications or a solution such as alcohol, which liquids can be used in the procedure for renal denervation. Thus, the Tuohy-Borst fitting with side arm at the guiding catheter's proximal end eliminates the need for a separate Tuohy-Borst "Y" adaptor and the three-way stopcock formed integral at the proximal end of the side arm tube eliminates the need to have that device separately attached to a Luer fitting at the proximal end of the side arm tube. Still further, the direction of the side arm tube relative to the guiding catheter tube being the same as the direction of the curved distal section of the guiding catheter allows the interventional cardiologist to easily find the correct azimuth angle around the circumference of the aorta for the easy placement of the distal end of the guiding catheter through the ostium of the renal artery.

Another novel feature of the present invention are markings on the outer cylindrical surface of the elongated hollow tube that constitutes most of the length of the guiding catheter. These markings are set at the distance to advance the guiding catheter through the patient's arterial system so that the distal end of the guiding catheter will be situated approximately 10±5 cm beyond the ostia of the renal arteries depending on the height of that patient. This can be accomplished because the distance from the skin at the groin entry site for the guiding catheter to the point at a 10±5 cm distance beyond the ostium of either renal artery is highly dependent upon how tall a particular patient would be.

Thus, it is an objective of the present invention to allow placement of a renal artery guiding catheter to have its distal end placed into the renal artery without requiring insertion of the guiding catheter through an introducer sheath thus allowing a smaller hole to be made in the wall of the femoral artery.

Another objective of this invention is to eliminate the need for a separate Tuohy-Borst "Y" adaptor by having a Tuohy-Borst fitting formed integral with the guiding catheter at the guiding catheter's proximal end.

Still another objective of the present invention is to have a side arm tube that has a three-way stopcock formed integral at the proximal end of that side arm tube thus eliminating the need for a separately attached three-way stopcock.

Still another objective of the present invention is to have a side arm tube that extends outward from the shaft of the guiding catheter so as to be co-planar with plane of the guiding catheter's curved distal section and also to be extending in the same direction as that curved distal section of the guiding catheter thus assisting the interventional cardiologist in placing the distal end of the guiding catheter into and through the ostium of a renal artery.

Still another objective of the invention is to use a guide wire and a dilator within a guiding catheter for placement of the guiding catheter without requiring an introducer sheath.

Still another objective of the invention is to utilize a dilator having a curved distal section that when placed inside a guiding catheter that has a curved dilator section in the opposite direction causes the dilator-guiding catheter assembly to be essentially straight for easy insertion through the arterial system.

Still another objective of the invention is to reduce the cost and time required for performing arterial interventional procedures for accessing the renal arteries by eliminating the need for an introducer sheath and by having a Tuohy-Borst fitting and a three-way stopcock each formed integral with the guiding catheter at its proximal end.

Still another objective of the invention is to reduce the probability of bleeding at the skin where the guiding catheter enters the femoral artery by eliminating the need for an introducer sheath to have the guiding catheter gain access to the patient's arterial system.

These and other objects and advantages of this invention will become obvious to a person of ordinary skill in this art upon reading of the detailed description of this invention including the associated drawings.

BRIEF DESCRIPTION OF THE DRAWINGS

FIG. 2 is a side view of the guiding catheter showing its curved distal section that occurs when the oppositely curved dilator is withdrawn.

FIG. 3 is a side view of a straightening dilator illustrating its curved distal section that curves opposite in its direction compared to the curved distal section of the guiding catheter into which the dilator is inserted so that the combination of both curves, as seen in FIG. 1, provides a comparatively straight distal section of the combined guiding catheter and straightening dilator for improved insertion through the patient's arterial system.

FIG. 7 illustrates the initial position of the distal ends of the guide wire, dilator and guiding catheter as they are initially inserted into the aorta just beyond the ostia of the left and right renal arteries.

FIG. 8 shows the initial position of the distal section of the guiding catheter within the aorta immediately after the guide wire and dilator have been withdrawn.

FIG. 9 shows the distal end of the guiding catheter placed into the renal artery after it has been pulled back from the position shown in FIG. 8.

DETAILED DESCRIPTION OF THE INVENTION

Figure 1:
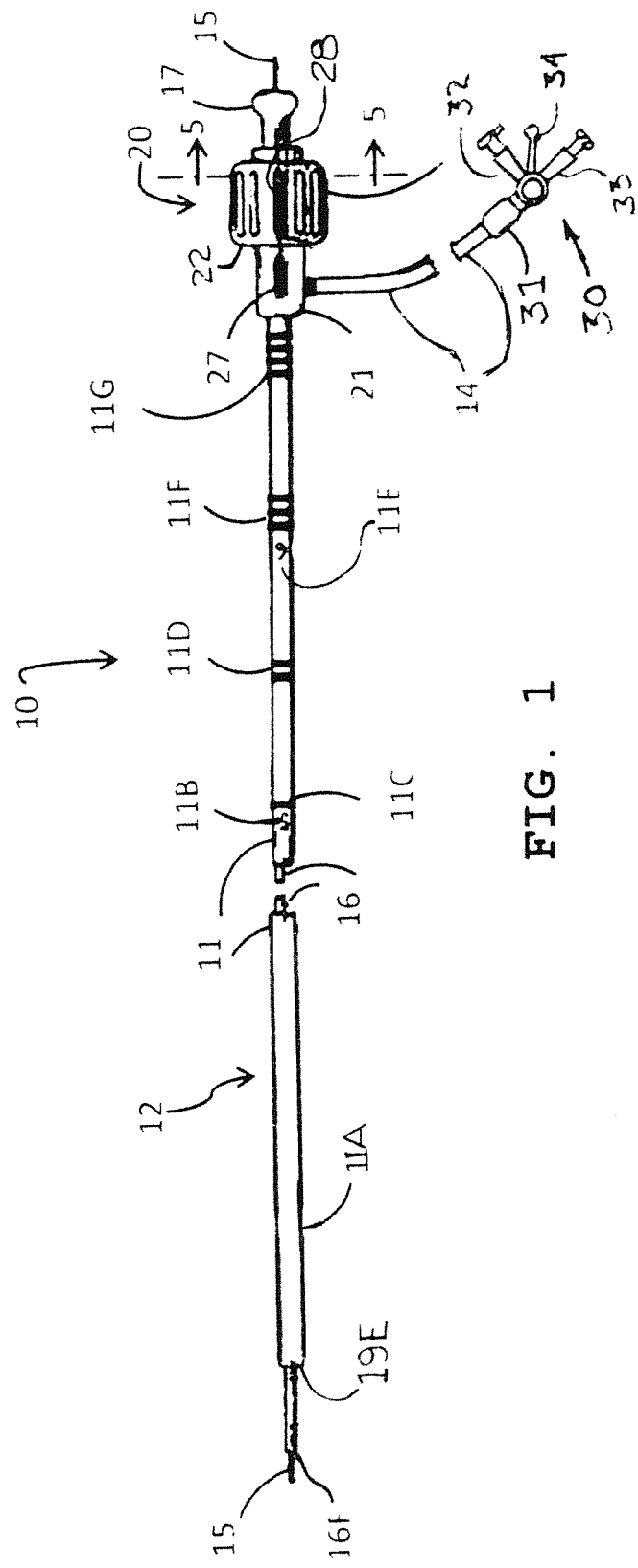
FIG. 1 is a side view of a guiding catheter system including a guide wire, straightening dilator and a guiding catheter with Tuohy-Borst fitting and a three-way stopcock mounted onto the side arm tube of the guiding catheter.

FIGS. 1, 2 and 3 illustrate the guiding catheter system 10 having a guiding catheter 12 with an elongated tube 11 with a distal section 11A having a distal end 19E, a Tuohy-Borst fitting 20, a side arm tube 14 with a three-way stopcock 30 at its proximal end, and a guide wire 15 and a straightening dilator 16 each situated within the tube 11. It should be noted that the configuration of FIG. 1 is how this guiding catheter system 10 would be placed through the patient's skin at the groin, then into the femoral artery and then advanced through the aorta and beyond the renal arteries as shown in FIG. 7.

As best seen in FIG. 2, the guiding catheter 12 has an elongated cylindrical tube 11 with a curved distal section 11A ending at point 19D where a short straight section 19S begins. The straight section 19S extends to its distal end 19E. It should be noted that the angle "a" that the centerline of the straight section 19S makes with the centerline of the straight section of the tube 11 should optimally be about 30 degrees. This angle "a" makes it possible for the straight section 19S to have a straight entry into a renal artery even if that renal artery makes a downward angle of as little as 30 degrees relative to the aorta. This is shown in greater detail with the assistance of FIG. 9.

The tube 11 also has markings 11B, 11C, 11D, 11E, 11F and 11G that indicate points on the tube 11 corresponding to how far the interventional cardiologist should advance the system 10 into the patient's arterial system depending on the height of the patient. The single line mark 11C indicates the extent to which the tube 11 should be advanced if the patient is approximately 5 feet tall. The number "5" (which is element 11B) reminds the cardiologist that the mark 11C corresponds to the point on the patient's skin at the groin to which the tube 11 should be advanced if the patient is approximately five feet tall. If the patient is 6 feet tall, as indicated by the "6" of element 11E, then the three lines of element 11F indicate the point to which the tube 11 should be advanced to place the mark 11F at the skin of the patient at his/her groin if that patient is six feet tall. The marks 11D and 11G correspond respectively to patient heights of five feet, six inches and six feet, six inches. For patient heights corresponding to a position between these markers, the cardiologist can set the depth to which the tube 11 is inserted through the patient's skin to be between the appropriate markers. For example, for a woman whose height is five feet, three inches, the tube 11 would be advanced through the patient's skin at her groin with the tube 11 placed at her skin halfway between the one line of mark 11C and the two lines of mark 11D. The approximate distance between each adjacent pair of the marks 11C, 11D, 11F and 11G would be 5±2 cm.

FIG. 2 also shows a proximal section of the guiding catheter 12 that has a threaded base 21, a threaded nut 22 and a side arm tube 14 that has a three-way stopcock 30 at its proximal end. When the marker 27 on the threaded base 21 is aligned with the marker 28 on the threaded nut 22, then the curved distal sections of the tube 11 and the dilator 16 will be 180 degrees in opposite directions and the distal curved sections 11A and 16A will act together to create a generally straight guiding catheter system 10 as shown in FIG. 1. This function will be described in greater detail with the assistance of FIGS. 3, 4 and 5 below.

As shown in FIG. 3, the dilator 16 has a distal curved section 16A that is connected to the straight section 16S at the point 16D, and the straight section 16S terminates at a tapered distal end 16E. The dilator tube 16 is designed to fit snugly around the guide wire 15. The dilator tube 16 is designed to be advanced over the guide wire 15 and within the lumen 13 of the guiding catheter tube 11 so that the assembly of the guiding catheter system 10 (as shown in FIG. 1) can be in a straightened condition so that it can be readily advanced through the patient's arterial system. All the sections of the dilator tube 16 are designed to fit slideably within the interior lumen 13 of the guiding catheter tube 11. It should be understood that there could be only one bend, or two or more bends at this distal section of the dilator tube 16 and the curved section 11A of the tube 11. The dilator also has at its proximal end a handle 17 with a cone 17A having a key 17B for mating with the keyway 26 of the threaded nut 22 of the Tuohy-Borst fitting 20 as seen in FIGS. 4 and 5.

Figure 4:
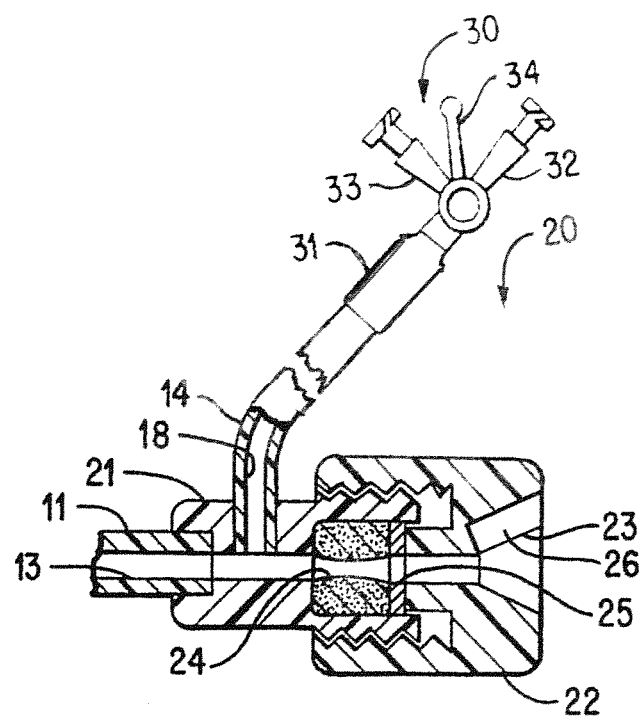
FIG. 4 is an enlarged partial longitudinal cross section of the proximal end of the guiding catheter at section 4-4 of FIG. 2.
Figure 5:
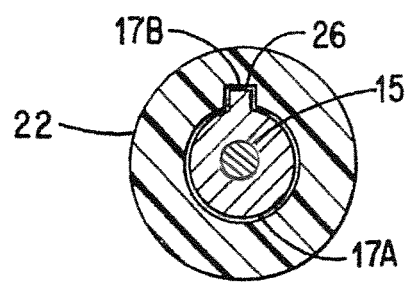
FIG. 5 is an enlarged transverse cross section of the Tuohy-Borst fitting at section 5-5 of FIG. 1.

As seen in FIGS. 1, 2 and 4, the guiding catheter 12 has a Tuohy-Borst fitting 20 that is integrally attached as a one-piece construction at the proximal end of the catheter tube 11. As best seen in FIG. 4, the Tuohy-Borst fitting 20 has a threaded base 21, a side arm 14 having a three-way stopcock 30 at its proximal end, a threaded nut 22 with conical entry lumen 23, a soft elastomer gland 24 and a comparatively hard washer 25. As seen in FIG. 4, when the nut 22 is not tightened down, the gland 24 is not compressed and the lumen 23 is in fluid communication with the lumen 13 of the elongated tube 11 and the lumen 18 of the side arm tube 14. When the nut 22 is screwed into the threaded base 21, the washer 25 compresses the soft elastomer gland 24 which can then fit snugly around a guide wire 15 or a dilator 16 or the shaft of a renal artery denervation catheter or a stent delivery catheter. Furthermore, when the nut 22 is fully screwed onto the threaded base 21, the central lumen of the gland 24 can be totally closed so that no blood will leak out of the guiding catheter's proximal end even if there is no guide wire 15 or catheter tube 11 placed through that gland 24.

As shown in FIGS. 1 and 2, the threaded base 21 has an indicator mark 27 which, when aligned with an indicator mark 28 on the nut 22, informs the operator that the tube 11 and the dilator 16 are positioned so that together they form a straight distal end section as shown in FIG. 1. It is also conceived that a straight dilator with a comparatively stiff distal section 16A could be used to straighten out the curved end section 11A of the guiding catheter 12 as is shown in FIG. 1. The stiffer the distal section of such a dilator 16, the straighter would be the distal section of the assembly of the dilator 16 with the guiding catheter 12. Of course, when such a straight (or curved) dilator would be pulled out, the distal section 11A of the guiding catheter 12 would assume its proper shape as generally illustrated in FIG. 2.

FIG. 4 shows the three-way stopcock 30 fixedly attached to the side arm tube 14 by means of the connecting tube 31. Specifically, FIG. 4 shows the stopcock 30 with an operating lever 34 in an intermediary position. For an external fluid source to connect to the lumen 18 by means of the Luer fitting 33, the lever 34 would be placed over the Luer fitting 32. For a fluid source to deliver fluid into the lumen 18 via the Luer fitting 32, the lever 34 would be placed over the Luer fitting 33. To close the side arm tube 14 from any access through either Luer fitting 32 or 33, the lever 34 would be placed over the connecting tube 31. It should be understood that a two-way or a four-way stopcock could be used instead of the three-way stopcock 30 shown in FIGS. 1 and 4. In general, a multi-way stopcock could be advantageously formed integral at the proximal end of the side arm tube 14.

FIGS. 4 and 5 also show a keyway 26 in the nut 22 which is adapted to mate with the key 17B of the dilator handle 17. When the marks 27 and 28 are aligned as shown in FIGS. 1 and 2, the alignment formed by keyway 26 and the key 17B guarantees that the bends in the distal sections of the guiding catheter tube 11 and the dilator 16 oppose each other so as to straighten the guiding catheter system 10 as shown in FIGS. 1 and 7. In this position, the guiding catheter 12 with dilator 16 in place can be readily advanced over the guide wire 15 until the distal end 19E of the guiding catheter tube 11 is located just beyond the ostium of the renal artery to which access is desired as is shown in FIG. 7. The dilator 16 and guide wire 15 can then be withdrawn and the guiding catheter 12 will assume its desired distal section shapes as shown in FIGS. 8 and 9. The cardiologist can then place the guiding catheter's distal end 19E through the ostium of a renal artery as shown in FIG. 9.

It is important to note that the guiding catheter system 10 should not be stored or packaged in the configuration as shown in FIG. 1. If that were to be done, then in time, and particularly if there is any exposure to an elevated temperature, the final distal section curve of the catheter tube 11 could be reduced and that would not be the optimum curve which is most suitable for accessing the renal arteries. If the package containing the system 10 was sold as shown in FIG. 1, then the final curvature at the distal section of the tube 11 could be considerably reduced as compared to the curve shown in FIG. 2. Therefore, the present invention conceives of the fact that the elements of the guiding catheter system 10 should be separated into a kit that at least allows the guiding catheter tube 11 and the dilator tube 16 to remain apart until the guiding catheter system 10 is assembled prior to insertion of the guiding catheter system 10 into the patient's arterial system.

Figure 6A:
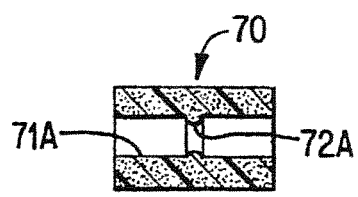
FIG. 6A is a cross section of a Tuohy-Borst gland with a half "O" ring with the gland in a fully open position.
Figure 6B:
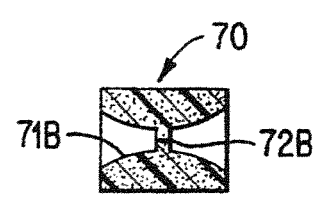
FIG. 6B is a cross section of a Tuohy-Borst gland with a half "O" ring with the gland in a fully closed position.

FIGS. 6A and 6B illustrate an alternative design for the soft elastomer gland of a Tuohy-Borst fitting 20. Specifically, FIG. 6A shows a gland 70 in its open (not compressed) state. The gland 70 has a generally cylindrical interior surface 71A on which is placed a half "O" ring 72A. When the nut 22 of FIG. 4 is tightened, the gland 70 can be deformed to the shape shown in FIG. 6B wherein a highly curved interior surface 71B is formed with the half "O" ring 72B being distorted to a closed or nearly closed position as shown in FIG. 6B.

FIGS. 7, 8 and 9 illustrate how the present invention would be used to effectively access either one or both of the renal arteries 82 and 83. FIG. 7 is a posterior view of certain body parts showing the aorta 80, the left kidney 81, the left renal artery 82, the right renal artery 83, the right kidney 84 and also the guiding catheter tube 11 in its straightened condition due to the insertion of the dilator 16 which was previously advanced with the guiding catheter 12 over the guide wire 15. It should be noted that the right renal artery 83 is typically longer than the left renal artery 82 due to the placement of the inferior vena cava between the aorta 80 and the right kidney 83. The distal end 85 of the guiding catheter tube 11 is shown in a position that is a length "D" beyond the centerline 85 of the ostia of the left and right renal arteries. An optimum distance for this distance D would be 10±5 cm. Thus, even if a patient of a particular height had his or her renal artery centerline further away from the entry of the guiding catheter system 10 at the patient's groin than that which is indicated by the marks 11B to 11H on the tube 11 (as shown in FIGS. 1 and 2) the distal end 19E of the tube 11 would still lie distinctly above the renal artery centerlines. It should be noted that the total length of the renal artery catheter 12 could optimally be approximately 60 cm. The distance from the catheter's distal end 19E to the first mark 11C (of FIGS. 1 and 2) being about 35±5 cm and the length from the distal end 19E to the mark 11G being approximately 50±5 cm. It should be noted that the mark 11C corresponds to a patient height of five feet and the mark 11G corresponds to a patient height of six feet, six inches. These lengths have been chosen so that at least a length of approximately 10 cm will typically be situated outside of the patient's skin at the groin irrespective of the patient's height. This 10 cm length provides the interventional cardiologist with additional margin for an extremely rare case when the renal arteries are even further away from the femoral artery entry point of the guiding catheter system 10 at the skin near the patient's groin.

After the guide wire 15 and the dilator 16 are withdrawn from the guiding catheter tube 11, the curved distal section 11A of the tube 11 would be situated as shown in FIG. 8. In this position, the distal end 19E of the curved distal section 11A of the catheter tube 11 would move against the wall of the aorta 80 opposite the wall where the tube 11 is situated. When that condition has been obtained, the cardiologist would typically inject contrast medium (not shown) through the three-way stopcock 30 to visualize the geometry of the ostium of the right renal artery 83. After that is accomplished, the cardiologist would pull back the proximal end of the guiding catheter 12 until the straight section 19S at the distal end of the curved distal section 11A enters into and through the ostium of the right renal artery 84 as shown in FIG. 9. It should be understood that the distal section 11A of the tube 11 would be made radiopaque so that it can be readily visualized by the interventional cardiologist using conventional image intensified fluoroscopy.

A unique feature of the present invention is that the interventional cardiologist could always get the straight section 19S to be aimed directly into the lumen of the renal artery irrespective of the angle that the renal artery typically makes with the aorta 80. This is certainly true for all angles "a" of the axis of a renal artery relative to the axis of the aorta (as shown in FIGS. 8 and 9) as normally found in human subjects. Particularly, any angle "a" between 90 degrees and 30 degrees downward could be readily accessed because of the shapes of the curved distal section 11A and the straight distal section 11S of the guiding catheter tube 11. The reason why this is the case is because, as the cardiologist pulls the guiding catheter tube 11 in a downward direction, the distal end 19E of the tube 11 will snap into and through the ostium of the renal artery into which it is aimed by means of the orientation of the side arm tube 14 at the proximal end of the guiding catheter 12. This is true because the straight section 19S will engage the point "p" (which is the apex of the angle "a") as the guiding catheter tube 11 is pulled downward through the aorta 80. The cardiologist can then adjust the position of the proximal end of the guiding catheter 12 so that the straight section 19S is aimed essentially straight into the right renal artery 83 as shown in FIG. 9. It is obvious that this technique can also be used to access either the right or the left renal artery.

The orientation of the side arm tube 14 that remains outside the patient's body will indicate to the cardiologist the correct angular orientation (i.e., the azimuth) of the curved distal section 11A and the straight section 19S at the distal portion of the guiding catheter tube 11. This is achievable because when the side arm tube 14 lies horizontally relative to the table on which the patient has been placed on his or her back, then the straight distal section 19S of the tube 11 will have the correct azimuth angle around the interior lumen of the aorta 80 in order to enter the correct renal artery. Thus when the side arm tube 14 would lie in a direction to the right and parallel to the operating table, then the distal end 19E of the tube 11 would enter the left renal artery 82. Likewise, if the side arm tube 14 is lying to the left and is parallel to the operating table, then the azimuth angle of the distal end 19E of the guiding catheter tube 11 will be correct for entering the right renal artery 83 as shown in FIG. 9.

This invention envisions that the Tuohy-Borst gland (such as glands 24 or 70) could be fabricated from a soft elastomer such as a low durometer silicone rubber. Furthermore, powdered Teflon or powdered graphite could be incorporated into the soft elastomer to improve its lubricity.

Thus the objectives of using a guiding catheter without passing it through an introducer sheath and the elimination of the need for a separate Tuohy-Borst "Y" adaptor and a separately attached three-way stopcock have been shown. Furthermore, the objective of inserting a guiding catheter and dilator over a guide wire without the free release of blood through the guiding catheter's proximal end can be accomplished by compressing the gland 24 around the guiding catheter tube 11 as the guiding catheter system 10 is advanced through the arterial system.

Although the discussion herein has been principally concerned with renal guiding catheter systems, the present invention is well suited for the placement of guiding catheters into the ostium of other arteries such as the carotid and coronary arteries as well as coronary artery bypass grafts.

Various other modifications, adaptations, and alternative designs are, of course, possible in light of the above teachings. Therefore, it should be understood at this time that within the scope of the appended claims, the invention may be practiced otherwise then as specifically described herein.

The invention claimed is:

1. A guiding catheter system for the insertion of a catheter into a renal artery, the system consisting of:
    a guiding catheter having an elongated hollow tube that has proximal and distal ends and a distal section, the distal section having a curved section and a straight section extending from the distal end of the curved section, the curved section and the straight section being shaped so as to facilitate introduction and retention of the guiding catheter's distal section into and through the ostium of a renal artery for any angle of the renal artery relative to the aorta that lies between 30 and 90 degrees;
    a dilator inserted into the guiding catheter's hollow tube with a curved distal section of the dilator being placed at 180 degrees opposite the curved distal section of the hollow tube of the guiding catheter so that the assembly of the guiding catheter and the dilator forms an essentially straight distal section;
    the guiding catheter having a side arm tube located near the guiding catheter's proximal end with a multi-way stopcock fixedly attached onto the proximal end of the side arm tube; and
    a backflow adapter fitted to the hollow tube at the proximal end of the guiding catheter, a side arm tube joined to a threaded base of the backflow adapter, the side arm tube extending outward from the threaded base in a direction that is substantially co-planar with the plane of the curved distal section of the hollow tube of the guiding catheter and the side arm tube extending in the same direction outward from the hollow tube of the guiding catheter as the curved distal section of the guiding catheter.

2. The guiding catheter system of claim 1 where the dilator has a central lumen for the placement of a guide wire through that central lumen.

3. The guiding catheter system of claim 1 where the multi-way stopcock is a three-way stopcock.

4. The guiding catheter system of claim 1 including the backflow adapter having a threaded nut and an elastomer gland that can be tightened around the dilator by screwing the threaded nut onto the threaded base.

5. The guiding catheter system of claim 1 where the total length of the guiding catheter is approximately 60+5 cm.

6. The guiding catheter system of claim 1, where the dilator includes a handle at its proximal end, the handle having a key that fits into a keyway in the threaded nut of the backflow adapter located at the proximal end of the guiding catheter, and the keyway being formed to cause the orientation of the curved distal section of the guiding catheter to be in the opposite direction as the curved distal section of the dilator thus providing a comparatively straight distal section for the guiding catheter system.

7. The guiding catheter system of claim 1 where the elongated hollow tube of the guiding catheter will assume a generally curved shape at its distal section when the dilator and guide wire are withdrawn from the interior lumen of the guiding catheter's hollow tube and the straight section at the distal end of the curved distal section will make an angle "a" relative to the longitudinal axis of the straight section of the elongated hollow tube and the angle "a" shall be between 30 and 45 degrees.

8. The guiding catheter system of claim 1 where the backflow adapter is a Tuohy-Borst fitting.

9. The guiding catheter system of claim 1 where the guiding catheter's hollow tube has markings on its external cylindrical surface that indicate the extent to which the guiding catheter should be inserted into the patient's arterial system depending upon the height of the patient into whose renal artery the distal end of the guiding catheter is being inserted.

10. The guiding catheter system of claim 9 where the markings are positionally located on said external cylindrical surface of said hollow tube as a function of the height of the patient into whom the guiding catheter system is to be inserted.

11. The guiding catheter system of claim 9 where the marks to indicate the patient's height extend over at least a range from five feet to six feet and six inches.

12. The guiding catheter system of claim 9 where the distance from the mark for the person who is five feet tall to the distal end of the hollow guiding catheter tube is approximately 35+5 cm.

13. The guiding catheter system of claim 9 where the distance between adjacent marks corresponding to a difference in height of the patient of six inches is a distance along the hollow tube of the guiding catheter of approximately 5+2 cm.

14. The guiding catheter system of claim 9 where the marks on the hollow guiding catheter tube include the number 5 to indicate a patient height of five feet and the number 6 to indicate a patient height of six feet.

15. The guiding catheter system of claim 1 where a gland of the backflow adapter is fabricated from a soft elastomer which elastomer includes powdered Teflon to improve lubricity of the gland.

16. The guiding catheter system of claim 1 where a gland of the backflow adapter is fabricated from a soft elastomer which elastomer includes a powdered graphite to improve lubricity of the gland.

17. A guiding catheter system for the insertion of a catheter into a renal artery, the system consisting of:
- a guiding catheter having an elongated hollow tube that has proximal and distal ends and a distal section, the distal section having a curved section and a straight section extending from the distal end of the curved section, the curved section and the straight section each being shaped so as to facilitate introduction and retention of the guiding catheter's distal section into and through the ostium of a renal artery irrespective of the angle of the renal artery relative to the aorta that lies between 30 and 90 degrees;
- a dilator inserted into the guiding catheter's hollow tube with a curved distal section of the dilator being placed at 180 degrees opposite the curved distal section of the hollow tube of the guiding catheter so that the assembly of the guiding catheter and the dilator forms an essentially straight distal section; and
- the guiding catheter having a side arm tube located near the guiding catheter's proximal end that is directed outwardly from the longitudinal axis of the guiding catheter's elongated hollow tube, the side arm tube being essentially co-planar with and in the same outward direction as the curved distal section of the guiding catheter.

18. A guiding catheter having a curved distal section that is designed for insertion into and through the ostium of a renal artery, the guiding catheter also having a straight cylindrical section that has marks on its outer cylindrical surface that indicate the extent to which the guiding catheter should be advanced into the patient's arterial system depending upon the height of the patient into whose arterial system the guiding catheter is inserted; and
- a backflow adapter fitted to a hollow tube at a proximal end of the guiding catheter, a side arm tube joined to a threaded base of the backflow adapter, the side arm tube extending outward from the threaded base in a direction that is substantially co-planar with the plane of the curved distal section of the hollow tube of the guiding catheter and the side arm tube extending in the same direction outward from the hollow tube of the guiding catheter as the curved distal section of the guiding catheter.

\* \* \* \* \*